United States Patent
Brown (10) Patent No.: US 9,000,332 B2
(45) Date of Patent: Apr. 7, 2015

(54) APPARATUS AND METHOD FOR HEATING AN ENDODONTIC INSTRUMENT BY INFRARED RADIATION

(71) Applicant: Erik Brown, Monrovia, CA (US)

(72) Inventor: Erik Brown, Monrovia, CA (US)

(73) Assignee: Ormco Corporation, Orange, CA (US)

( * ) Notice: Subject to any disclaimer, the term of this patent is extended or adjusted under 35 U.S.C. 154(b) by 0 days.

(21) Appl. No.: 14/041,812

(22) Filed: Sep. 30, 2013

(65) Prior Publication Data

US 2014/0030677 A1 Jan. 30, 2014

Related U.S. Application Data

(62) Division of application No. 13/410,832, filed on Mar. 2, 2012.

(51) Int. Cl.
- A61C 5/04 (2006.01)
- B29C 65/14 (2006.01)
- F27D 1/00 (2006.01)

(52) U.S. Cl.
CPC ............. *A61C 5/045* (2013.01); *B29C 65/1412* (2013.01)

(58) Field of Classification Search
None
See application file for complete search history.

(56) References Cited

U.S. PATENT DOCUMENTS

| | | | |
|---|---|---|---|
| 1,234,499 A | 7/1917 | Smalley | |
| 1,730,373 A * | 10/1929 | Kideney | 607/80 |
| 2,076,485 A * | 4/1937 | Streysman et al. | 219/521 |
| 2,271,485 A | 1/1942 | Koci | |
| 2,282,070 A * | 5/1942 | Mahannah | 34/660 |
| 2,426,976 A | 9/1947 | Taulman | |
| 2,836,696 A * | 5/1958 | Ratchford | 219/390 |
| 3,396,455 A | 8/1968 | Sherlock | |
| 3,466,752 A * | 9/1969 | Braun | 433/32 |
| 3,548,146 A | 12/1970 | Hoyland | |
| 3,640,001 A * | 2/1972 | Ellison | 34/218 |
| 4,460,820 A | 7/1984 | Matsumoto et al. | |
| 4,481,405 A * | 11/1984 | Malick | 219/405 |
| 4,558,203 A | 12/1985 | Bauridl | |
| 4,558,660 A | 12/1985 | Nishizawa et al. | |
| 4,621,187 A | 11/1986 | Petro, Jr. | |
| 5,028,228 A * | 7/1991 | Ubukata et al. | 425/298 |
| 5,060,289 A * | 10/1991 | Abramson | 392/423 |
| 5,061,411 A * | 10/1991 | Ubukata et al. | 264/16 |
| 5,181,455 A | 1/1993 | Masel et al. | |
| 5,215,461 A * | 6/1993 | Riazi | 433/224 |
| 5,286,423 A * | 2/1994 | Johnson | 264/16 |
| 5,372,759 A * | 12/1994 | Johnson | 264/16 |
| 5,384,889 A * | 1/1995 | Cook | 392/416 |

(Continued)

OTHER PUBLICATIONS

Dentsply Tulsa Dental Specialities, WaveOne™ Reciprocating File, undated.

(Continued)

*Primary Examiner* — Joseph M Pelham
(74) *Attorney, Agent, or Firm* — Wood, Herron & Evans, LLP (57) ABSTRACT

An apparatus and method for heating an endodontic instrument by infrared radiation includes a housing defining a chamber. An infrared heating element is positioned within the chamber. The housing includes an aperture and an adjacent holder for holding the endodontic instrument, such as an obturator. The endodontic instrument held by the holder extends through the aperture and into the chamber. The infrared heating element directs infrared radiation toward the endodontic instrument, which heats the endodontic instrument.

21 Claims, 3 Drawing Sheets

(56) References Cited

U.S. PATENT DOCUMENTS

| | | | |
|---|---|---|---|
| 5,404,420 A | 4/1995 | Song | |
| 5,575,196 A * | 11/1996 | Masel et al. | 99/421 V |
| 5,586,488 A | 12/1996 | Liu | |
| 6,002,110 A * | 12/1999 | Sikka et al. | 219/411 |
| 6,236,020 B1 * | 5/2001 | Friedman | 219/385 |
| 6,252,202 B1 | 6/2001 | Zychek | |
| 6,281,476 B1 | 8/2001 | Voizey | |
| 6,320,162 B1 * | 11/2001 | Friedman | 219/385 |
| 6,384,381 B2 | 5/2002 | Witt et al. | |
| 6,426,486 B1 | 7/2002 | Bartok | |
| 6,854,380 B2 | 2/2005 | Wanat | |
| 6,863,864 B1 | 3/2005 | Ingemanson | |
| 7,002,107 B2 | 2/2006 | Nooh | |
| 7,015,423 B2 * | 3/2006 | Friedman | 219/385 |
| 7,133,606 B1 | 11/2006 | Elliott et al. | |
| 7,230,208 B2 | 6/2007 | Miller | |
| 7,570,875 B1 * | 8/2009 | Groves et al. | 392/411 |
| 7,665,991 B1 | 2/2010 | Kert | |
| 7,853,128 B2 | 12/2010 | Cavada et al. | |
| 2004/0211324 A1 | 10/2004 | Wanat | |
| 2008/0037965 A1 * | 2/2008 | De Luca | 392/416 |
| 2009/0023115 A1 * | 1/2009 | Bohner et al. | 433/228.1 |
| 2011/0266271 A1 | 11/2011 | Boyer et al. | |
| 2013/0230821 A1 * | 9/2013 | Brown | 433/29 |
| 2014/0212829 A1 * | 7/2014 | Van Den Houdt et al. | 433/27 |

OTHER PUBLICATIONS

Dentsply Tulsa Dental Specialities, GT Series Obturators, 2007.
CMS Dental, Soft-Core Endodontic Obturator Oven, website, Aug. 24, 2011.
U.S. Patent and Trademark Office, Restriction Requirement issued in U.S. Appl. No. 13/410,832, dated Dec. 4, 2012 (5 pages).
U.S. Patent and Trademark Office, Office Action issued in parent U.S. Appl. No. 13/410,832, dated Jun. 4, 2013 (13 pages).

* cited by examiner

APPARATUS AND METHOD FOR HEATING AN ENDODONTIC INSTRUMENT BY INFRARED RADIATION

CROSS REFERENCE TO RELATED APPLICATIONS

This application is a divisional of U.S. patent application Ser. No. 13/410,832, filed Mar. 2, 2012, the disclosure of which is incorporated by reference herein in its entirety.

TECHNICAL FIELD

The present invention relates generally to an apparatus and method for heating an endodontic instrument, and more particularly, to heating an endodontic instrument such as an obturator for treating root canal cavities.

BACKGROUND

Root canal therapy may be completed in essentially a three step process. First, a dentist, endodontist, or other medical practitioner mechanically removes infected pulp from within the internal root structure of a tooth. Second, the internal root structure is cleaned and disinfected leaving a void in the place of the infected pulp. Third, the void is obturated or filled with a biocompatible, semi-structural material.

The voids created within root canal systems during such a root canal therapy often present highly complex geometries which vary significantly from treatment to treatment. Traditionally during the obturation step, the root canal receives gutta percha, RESILON®, or similar material in a softened and highly viscous condition. The gutta percha then hardens within the enlarged and cleaned root canals, while retaining some resiliency to sufficiently fill the complex voids. However, the expertise required for such traditional obturation requires significant equipment and many additional procedural steps.

Therefore, to simplify obturation, there is a growing trend in root canal therapy to make use of so-called "obturators." Obturators are essentially a toothpick sized stick of root canal filling material. During the procedure, the practitioner places the obturator in a small oven to warm and soften the filling material. Once properly heated, the obturator is used to conform the softened filling material to the complex geometries of the root canal structure and eventually fill the remaining void. Due to the inherent simplicity of an obturator relative to more traditional methods, it has become clinically accepted that obturators allow practitioners to achieve greater success rates with patient root canal therapies. Thus, patients benefit from less pain and infection while practitioners benefit from less equipment and decreased procedure complexity.

Despite these beneficial outcomes, the acceptance of obturators amongst practitioners has been hindered by at least three attributes of the small ovens used to heat the obturators. First and foremost, these ovens require considerable time to "pre-heat" before use. Pre-heating requires the practitioner or other office clinician to carefully plan ahead while simultaneously performing the procedure, thereby creating additional complexity in what may be an already busy office environment. Secondly, once the oven is pre-heated, the obturator must be placed in the oven and heated to the proper temperature. Heating the obturator is a relatively time-consuming process that can only be minimized with excellent planning on the part of the practitioner. Finally, powering the oven includes a cord which must be plugged into a nearby power outlet, which limits the locations in which the oven may be operated. Moreover, any mistake on the part of the practitioner or other office clinician in attempting to accommodate this complexity results in idle time and decreased efficiency.

Presently, ovens used in conjunction with obturators rely on natural convective heating. The heat is generated by a resistive heating coil element generally heated from 120° C. to 180° C. After the obturator is placed within the oven, it is slowly raised to the proper temperature via convective heating by the warmed air flowing around the obturator. Unfortunately, the time and complexity required to use these convective ovens has hindered the wide use of obturators in practice to the detriment of practitioners and patients alike.

There is a need for an apparatus and method for use in endodontic procedures, such as root canal therapy, that addresses present challenges and characteristics such as those discussed above.

SUMMARY

In one embodiment, the invention provides an apparatus for heating and softening a filling material portion of an endodontic instrument by infrared radiation. The apparatus generally comprises a housing defining a chamber and an infrared heating element within the chamber configured to generate heat energy. The housing of the chamber includes an aperture. Adjacent to the housing is a holder configured to hold the endodontic instrument such that at least the filling material portion of the endodontic instrument extends through the aperture and into the chamber for receiving the heat energy generated by the infrared heating element. The axis of the aperture is aligned with a central portion of the chamber along an instrument axis. The infrared radiation is directed along the instrument axis.

Various additional aspects of the apparatus include a heat sink adjacent to the housing that is configured to dissipate a portion of the heat energy. The housing also includes air vents configured to dissipate a portion of the heat energy. Moreover, a reflective surface is adjacent to the chamber and configured to direct at least a portion of the heat energy from the infrared heating element toward the filling material of the endodontic instrument extending into the chamber.

In yet another embodiment of the invention, the apparatus comprises a core structure and a housing that includes a top cover and a bottom such that an infrared heating element is interposed between the top cover and the bottom and within the core structure. The top cover, bottom, and core structure thereby define a chamber. Within the top cover is an aperture. Adjacent to the top cover is a holder configured to hold the endodontic instrument extending through the aperture and into the chamber.

As to using an embodiment of the invention, the endodontic instrument is held such that at least a portion of the filling material of the endodontic instrument extends into the chamber. Within the chamber, infrared radiation is directed at the filling material. The radiation heats and softens the filling material so that the practitioner is capable of filling the root canal with the softened filling material portion of the endodontic instrument.

Various additional objectives, advantages, and features of the invention will be appreciated from a review of the following detailed description of the illustrative embodiments taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

Figure 1:
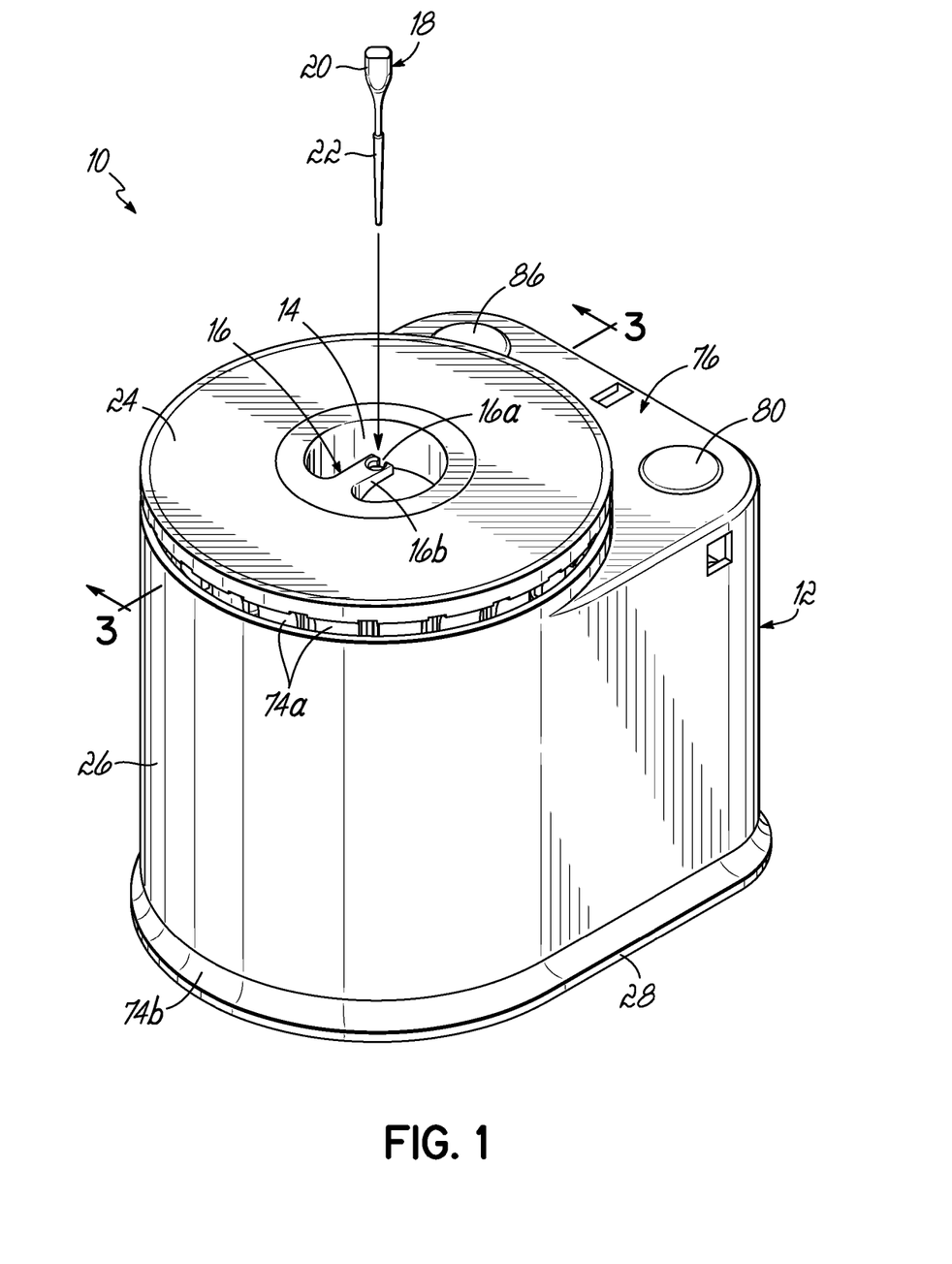
FIG. 1 is a perspective view of the apparatus for heating an endodontic instrument by infrared radiation according to an embodiment of the invention.

With reference to FIG. 1, an embodiment of the apparatus 10 for heating an endodontic instrument by infrared radiation includes a housing 12, an aperture 14 through the housing 12, and a holder 16 configured for use with an endodontic instrument. In the preferred embodiment of FIG. 1, the endodontic instrument is an obturator 18; however, any endodontic instrument to be heated may be used with the apparatus 10. As such, the obturator 18 includes both a handle 20 and a filling material 22.

Various alternatives to infrared radiation were considered for the apparatus 10; however, further research found these alternatives deficient in comparison to infrared radiation. Several alternatives included forced convective heating, inductive heating, and microwave heating.

Similar to an industrial heat gun, forced convective heating would generate a super-heated vortex of air within the apparatus 10 directed toward the target, obturator 18. This vortex of swirling air would surround and controllably heat the filling material 22 according to several properties including the air temperature of the vortex, the rate of convection, and pattern of the vortex. Despite the ability to control these properties, forced convective heating proved relatively time sensitive and costly. For instance, decreasing the time to heat the filling material 22 required superheating the air within the apparatus 10, which required additional time to pre-heat the air. Moreover, once the filling material 22 was properly heated and the apparatus 10 was powered off, the super-heated air remaining within the apparatus 10 would continue to heat the filling material 22. Thereby, the filling material 22 would be at a relatively high risk of overheating. Finally, throughout this heating process, the relatively large vortex of super-heated air preferably should be sealed within the apparatus 10 to reduce the risk of exposure to the operator. Sealing the apparatus 10 would greatly increase the cost of the apparatus 10. Thus, forced convective heating proved considerably time sensitive and costly.

Inductive heating has also been used in targeted heating applications. Inductive heating would focus a rapidly fluctuating electromagnetic field at the obturator 18 to induce an oscillating electrical current. In turn, resistance to the electrical current within the filling material 22 generates heat therein. However, in this application, the filling material 22 lacks sufficient conductivity for a reasonably sized apparatus 10 to efficiently heat the filling material 22.

Microwave heating of targeted objects, such as obturator 18, has also been considered, but been dismissed for material deficiencies of the filling material 22. Microwave energy typically heats an object which includes water, fats, or sugar molecules. Because the filling material 22 does not include these molecules, microwave energy simply passes through the filling material 22 without generating significant heat. While the filling material 22 could be reformulated to include these molecules, downstream complications could negatively impact the effective use of the obturator 18 in practice.

In view of these alternative technologies, infrared radiation overcomes these deficiencies in several respects. First, a source of the infrared radiation is readily controllable by the application of electrical current. Second, the application and removal of electrical current relatively instantaneously turns on and off the infrared radiation, which greatly reduces the time to pre-heat the apparatus 10 while reducing the risk of overheating the filling material 22. Third, the filling material 22 readily absorbs infrared radiation promoting efficient heating in present practice. Fourth, sources of infrared radiation are typically solid state, readily available, relatively low cost, and highly reliable. Thus, despite additional challenges to infrared radiation discussed herein, infrared radiation has proven to be the preferred alternative to heat the filling material 22.

In one aspect of the embodiment, the housing 12 forms the exterior of the apparatus 10 so as to insulate an operator from the heat produced therein. Thus, in a preferred embodiment, the material of the housing 12 is plastic or similar thermally insulating material. The housing 12 is generally cylindrical with rounded sides and sufficiently flat upper and lower surfaces. Sufficiently flat lower surfaces provide sturdy support for resting the apparatus 10 on a desk, counter, or other location convenient for the operator. In another aspect of the embodiment, near the top of the housing 12 is an aperture 14. The aperture 14 extends through the top of the housing 12 and permits access to the interior of the apparatus 10. Sufficiently flat upper surfaces make the aperture 14 more apparent and convenient for use with the obturator 18. As shown by FIG. 1, the obturator 18 is inserted into the aperture 14 so that heat generated within the interior of the apparatus 10 is directed to the obturator 18 while the housing 12 insulates this heat from a nearby operator.

In another aspect of the embodiment shown in FIG. 1, a holder 16 is configured to hold the obturator 18. The holder 16 is adjacent to the housing 12 and aperture 14 thereby holding the obturator 18 in a position such that the obturator 18 to extends within the interior of the apparatus 10. In a preferred embodiment, the holder 16 is positioned above the aperture 14 so that the obturator 18 dangles within this interior under the influence of gravity. Generally, the obturator 18 includes the handle 20 for gripping and a toothpick-sized stick of the filling material 22 connected thereto. The obturator 18 is positioned on the holder 16 such that the filling material 22 extends into the interior of the apparatus 10. The holder 16 may be in the form of a hook, hole, channel, slot, or any such structure 16a capable of holding the obturator 18. Moreover, the handle 20 is larger than the structure 16a for holding the obturator 18. Thus, the handle 20 of the obturator 18 is properly positioned by the holder 16 without falling into the apparatus 10.

Figure 2:
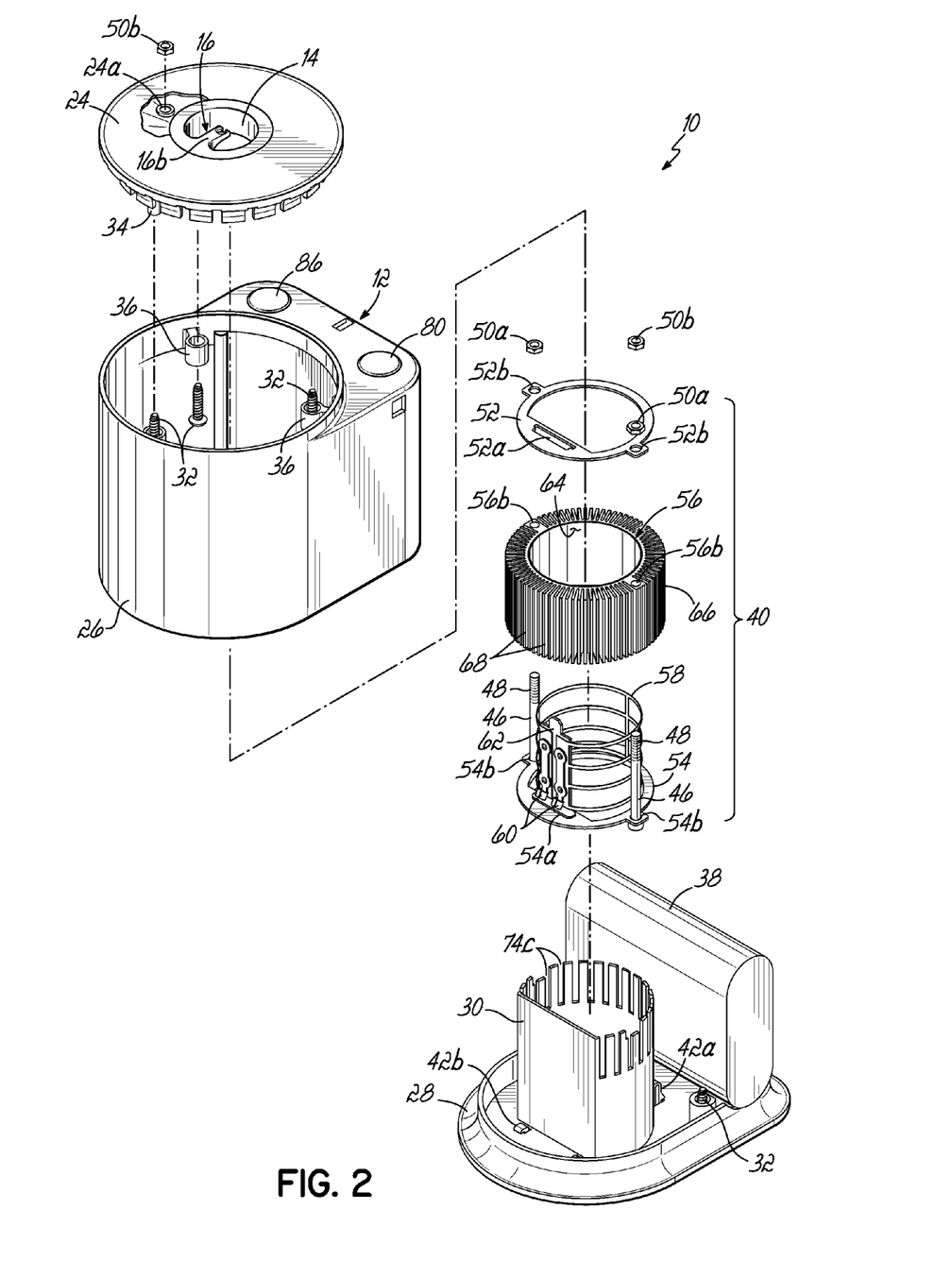
FIG. 2 is an exploded perspective view of FIG. 1.
Figure 3:
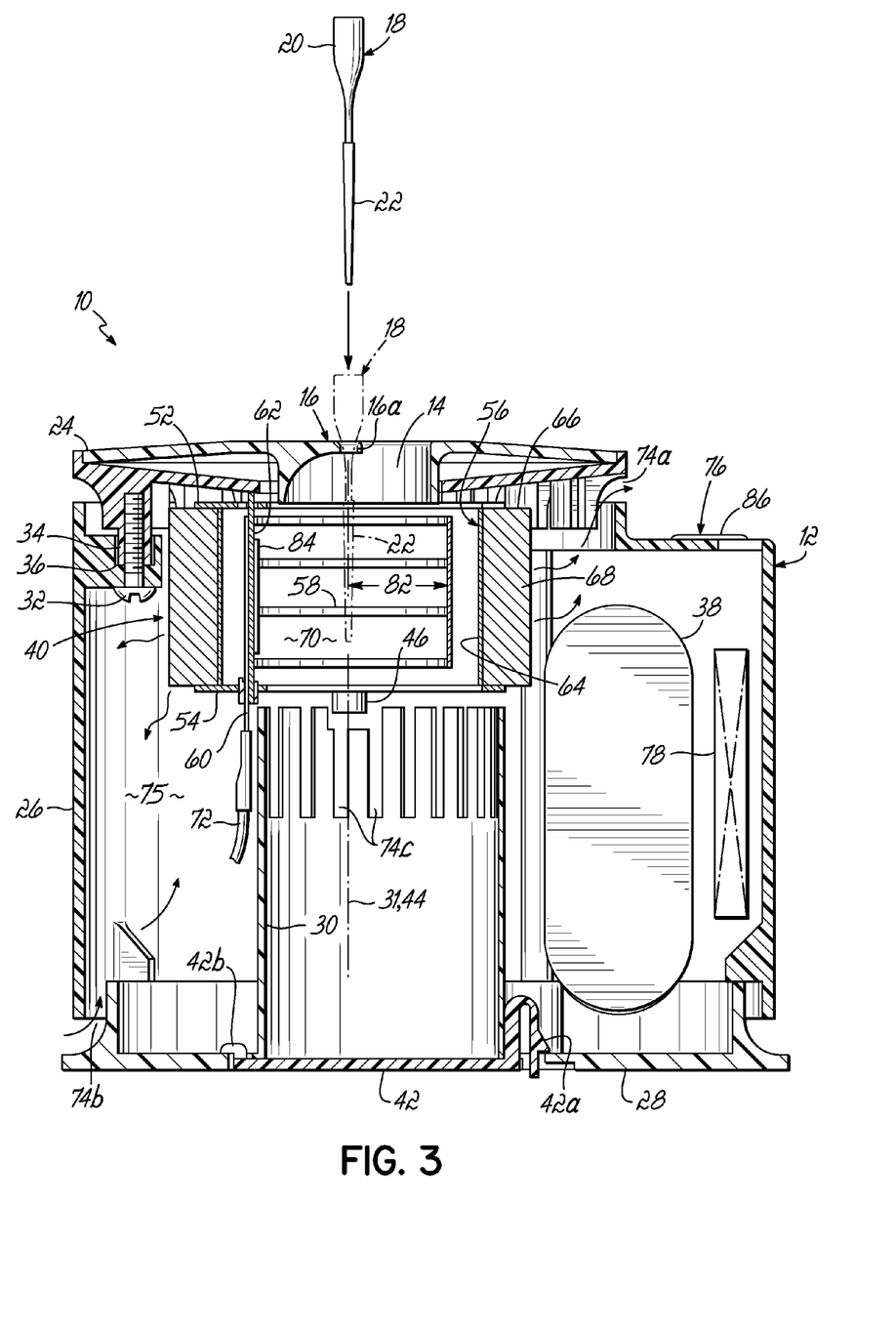
FIG. 3 is a cross sectional view taken on line 3-3 of the apparatus of FIG. 1.

As shown by the embodiment in FIG. 2 and FIG. 3, the housing 12 includes a top cover 24, central body 26, bottom 28, and heater well 30. In one aspect, the top cover 24 includes the aperture 14. In a preferred embodiment, the top cover 24 also includes the adjacent holder 16. The holder 16 is a circular ring with a hole therethrough concentrically aligning with the aperture 14. The holder 16 is positioned within the top cover 24. The holder 16 and top cover 24 are formed separately and assembled. In one aspect of the embodiment as shown, the holder 16 is formed from material with improved resistance to heat while the top cover 24 is formed from preferably less expensive material. Alternatively, the holder 16 and the top cover 24 may be formed as a single unit. Additionally, a tab 16b extends from the circular ring, to which it is attached, to an axis 31 of the aperture 14. At the end of the tab 16b and through the axis 31 of the aperture 14 is the hook 16a configured to grip the obturator 18. Thus, the obturator 18 is placed on the holder 16 and along the axis 31 of the aperture 14.

The top cover 24 is secured to the central body 26 of the housing 12. The top cover 24 is secured to the central body 26 by a fastener 32 through a dowel 34 and a dowel hole 36. The dowel 34 and dowel hole 36 aid in assembly and further limit relative movement. As shown in FIG. 2, the plurality of dowels 34 and dowel holes 36 include the plurality of fasteners 32 therethrough to secure the top cover 24 to the central body 26. More specifically, a set of three dowels 34, dowel holes 36, and fasteners 32 are so used.

The central body 26 is secured to the bottom 28 of the housing 12 by way of fasteners 32, as best shown in FIG. 2. The top cover 24, the central body 26, the bottom 28, and the heater well 30 serve to define the interior of the housing 12 that houses a battery 38 and a heating unit 40. More specifically, the battery 38 is a lithium-ion battery 38; however, any source capable of providing power to the apparatus 10 may be used. Furthermore, the battery 38 is attached to the bottom 28.

The heater well 30 is positioned below the heating unit 40 and integrally formed with the bottom 28. The heater well 30 includes a walled periphery with an open top and a generally solid, planar removable cover 42 placed adjacent to the bottom 28. The heater well 30 serves to collect obturators 18 accidentally dropped by the operator through the aperture 14. The heater well 30 proves useful for collecting dropped obturators 18 in a location relatively apart from the heating unit 40. In addition, the removable cover 42 includes a snap 42a and a clip 42b for removably attaching the removable cover 42 in the proper position covering the heater well 30 as shown in FIG. 3. Two clips 42b are inserted into matching slots within the bottom 28. Once the clips 42b are so inserted, the removable cover 42 can swing such that the snap 42a is placed adjacent to the bottom 28 and snapped into place. In the event the obturator 18 drops through the aperture 14, the operator may then retrieve obturators 18 collected within the heater well 30 by removing the removable cover 42 from the apparatus 10, discarding the collected obturators 18, and reinstalling the removable cover 42 into the heater well 30.

The heating unit 40 is mounted above heater well 30 to the top cover 24 so that an instrument axis 44 of the heating unit 40 is aligned with the axis 31 of the aperture 14. The instrument axis 44 is centrally located within the heating unit 40 and preferably passes vertically through a central portion of the heating unit 40. The mounting of the heating unit 40 is attached to and below the top cover 24 by a core fastener 46. As shown in FIG. 2 and FIG. 3, the core fastener 46 acts as a tie rod to compress the heating unit 40 together. The core fastener 46 extends through the heating unit 40 exposing a screwthread 48 onto which a lower nut 50a is tightened, thereby compressing the heating unit 40. The top cover 24 includes a mounting boss 24a into which screwthread 48 is inserted. An upper nut 50b is also tightened onto the screwthread 48 which affixes the top cover 24 to the heating unit 40. More specifically, a pair of the core fasteners 46 and mounting bosses 24a are so used. For exemplary purposes, only one mounting boss 24a is shown in FIG. 2. The heating unit 40 is affixed to and below the top cover 24 such that the obturator 18 extends through the top cover 24, along the instrument axis 44, and into heating unit 40.

According to the embodiments shown in FIGS. 1-3, the heating unit 40 includes a top plate 52, a bottom plate 54, a core structure 56, and an infrared heating element 58 with electrical connectors 60 attached at a stand 62. The core structure 56 is generally cylindrical and sandwiched between the top plate 52 and the bottom plate 54 by the core fasteners 46. The infrared heating element 58 is generally cylindrical as well, but, in addition, includes a generally planar portion at its periphery where the infrared heating element 58 accommodates the stand 62. Furthermore, the core structure 56 has a hollow, annular interior defining an interior surface and an interior void in which the infrared heating element 58 is positioned. The top plate 52 and the bottom plate 54 each include an opening 52a, 54a interior of the core structure 56 for receiving the stand 62. Moreover, the top plate 52, the bottom plate 54, and the core structure 56 each include a pair of fastener holes 52b, 54b, 56b for receiving core fasteners 46. In a preferred embodiment, the infrared heating element 58 is mounted to the stand 62, which is held between the bottom plate 54 and top plate 52 adjoined by the pair of core fasteners 46 within the core structure 56.

The infrared heating element 58 is an annular ribbon extending in a vertical direction along the hollow annular interior of the core structure 56. Moreover, to manufacture the annular ribbon, the infrared heating element 58 is stamped from a continuous sheet of a suitable material and then rolled into the generally cylindrical shape, more specifically the annular ribbon. This is in contrast to a traditional infrared heating element which consists of coils. Moreover, the suitable material produces heat energy when subjected to an electrical current. At least a portion of the heat energy produced by the electrical current is infrared radiation. For example, such a suitable material is nichrome consisting of 80% nickel and 20% chromium. Once rolled, the infrared heating element 58 is crimped to the stand 62. Moreover, the stand 62 includes tabs that insert into the openings 52a, 54a of bottom plate 54 and the top plate 52 to hold the stand 62 and connected infrared heating element 58 in position. In addition, the stand 62 is formed of electrically insulated material capable of withstanding the heat produced by the infrared heating element 58. For example, the stand 62 preferably consists of mica.

In a preferred embodiment, at least a portion of the heat generated by the infrared heating element 58 is managed by the heating unit 40 with a reflective surface 64. The reflective surface 64 is positioned within the hollow annular interior of the core structure 56 and adjacent to the infrared heating element 58. The reflective surface 64 at least partially surrounds the infrared heating element 58 and the instrument axis 44 of the heating unit 40. In a more preferred embodiment, the reflective surface 64 is positioned between the interior surface of the core structure 56 and the infrared heating element 58. More specifically, the interior surface is the reflective surface 64. The reflective surface 64 is configured to direct at least a portion of the heat generated by the infrared heating element 58 away from the core structure 56 and along the instrument axis 44 of the heating unit 40.

Another portion of the heat generated by the infrared heating element 58 will be absorbed by the heating unit 40 and the air within the heating unit 40 rather than directed by the reflective surface 64. This absorption and increase in air temperature results in a portion of the heat energy within the heating unit 40 preferably being dissipated to an ambient environment. Thus, the heating unit 40 also includes a heat sink 66 to decrease the temperature of the heating unit 40. The heat sink 66 includes a plurality of fins 68 affixed annularly to the exterior of the core structure 56. In addition, the heat sink 66 is thermally coupled between the heating unit 40 and the ambient environment to dissipate a portion of the heat generated from within the heating unit 40 to the ambient environment. The heat sink 66 is composed of material especially suitable for dissipating heat, such as aluminum. In a more preferred embodiment, the heat sink 66, the core structure 56, and the reflective surface 64 are formed as a unified component. Alternatively, the heat sink 66, the core structure 56, and the reflective surface 64 may be formed separately.

With reference to FIG. 3, the housing 12 defines a chamber 70 in which the infrared heating element 58 is positioned. The chamber 70 is further defined by the heating unit 40 or, more specifically, as the hollow within the core structure 56.

As shown in FIG. 3, an operator positions the obturator 18 onto holder 16 such that the obturator 18 extends downward into the chamber 70. In this orientation, the filling material 22 of the obturator 18 is within the chamber 70; however, the handle 20 of the obturator 18 may or may not be entirely within the chamber 70. Preferably, the handle 20 is not within the chamber 70 so that the operator may safely touch the handle 20 after heating the obturator 18. Within the chamber 70, the filling material 22 receives the heat energy generated by the infrared heating element 58, which softens the filling material 22 for root canal therapy.

Within the chamber 70, the filling material 22 of the obturator 18 is placed along the instrument axis 44 of the heating unit 40. In one aspect of the embodiment, the infrared heating element 58 extends at least partially around this instrument axis 44. In another aspect, the infrared heating element 58 is annular and extends coaxially around this instrument axis 44. Furthermore, the infrared heating element 58 is operatively connected to the electrical connectors 60 to a power cord 72. The power cord 72 delivers electrical power to the infrared heating element 58 by way of the operatively connected battery 38. However, it should be noted that any other power source, such as any standard wall outlet, may be used to provide power to the apparatus 10.

Still referring to FIG. 3, as power is delivered to the infrared heating element 58, infrared radiation is directed at the obturator 18 within the chamber 70. The filling material 22 absorbs the infrared radiation thereby increasing its temperature. However, the power delivered to the infrared heating element 58 increases the temperature of the infrared heating element 58. Moreover, infrared radiation is also absorbed by other components within the apparatus 10. For instance, the materials of the infrared heating element 58, the housing 12, the core structure 56, and other components of the heating unit 40 may each absorb infrared radiation. Thereby, the increased temperatures of these components, particularly the infrared heating element 58, generate convective heat. For this reason, the infrared heating element 58 produces heat from infrared radiation and heat from convection or, as otherwise referred to herein, infrared heat and convective heat, respectively.

In order to minimize the convective heat and maximize the infrared radiation directed toward the filling material 22, the reflective surface 64 at least partially surrounds the adjacent infrared heating element 58. The reflective surface 64 is configured to direct the infrared radiation toward the obturator 18, thus increasing the speed and efficiency with which the apparatus 10 heats the obturator 18 to the proper temperature while minimizing the production of convective heat with other components.

Management of the convective heat produced with the infrared heating element 58 is shown in further detail within FIG. 3. Heat sink 66, which is adjacent to the chamber 70 and in thermal communication with the chamber 70, absorbs excess convective heat for dissipation into the relatively cooler ambient environment. This dissipation of heat into ambient air forces relatively hot air to rise and exit an upper air vent 74a located adjacent to and within the top cover 24 of the apparatus 10. As hot air exits the apparatus 10, a vacuum is created in an interior space 75 within the housing 12 which draws cool air into a lower air vent 74b located near the bottom 28 of the apparatus 10. In one aspect of embodiment, the upper and lower air vents 74a, 74b, are annular passageways surrounding the upper and lower portions of the apparatus 10. More specifically, the upper and lower air vents 74a and 74b are formed as gaps between the central body 26 and the top cover 24 and bottom 28, respectively. Furthermore, the heater well 30 includes an internal air vent 74c to promote circulation of cool ambient air around the heating unit 40. In one aspect, the internal air vents 74c in the heater well 30 are gaps near the open top within the walled periphery to allow air below the heating unit 40 to circulate. Hot air within the chamber 70 and housing 12 is therefore exchanged for cooler ambient air to help maintain acceptable temperatures.

In another aspect of the embodiment shown in FIG. 3, the chamber 70 is sized with relatively large dimensions and a relatively large volume in relation to the obturator 18. More specifically, a relatively small chamber 70 would make it unnecessarily difficult for an operator to insert the obturator 18 into the chamber 70 without contacting and damaging nearby components, such as the infrared heating element 58. To protect the infrared heating element 58, the chamber 70 may include a glass shield (not shown) adjacent to the infrared heating element 58. However, such a glass shield decreases the efficiency of the apparatus 10. Thus, in the more preferred embodiment of FIGS. 1-3, the volume of the chamber 70 is large enough to prevent contact without the inclusion of the glass shield. Thereby, components are placed a substantial distance from the obturator 18 being inserted through the aperture 14 and into the heating unit 40, which decreases the likelihood of unintended damage from the operator and increasing efficiency of the apparatus 10.

As shown in FIGS. 1-3, the apparatus 10 includes controls for the operator to use in operation. These controls include a user interface 76 and a CPU 78. The battery 38 provides the power to operate the controls. In one aspect of the controls, the operator turns on the apparatus 10 by operating a control element 80. More specifically, the control element 80 is a button 80 that is pushed to turn on the apparatus 10; however, any control element 80 may be so used. Once the apparatus 10 is operational, the infrared heating element 58 heats to the predetermined temperature and remains on a predetermined amount of time, until the filling material 22 is properly softened by the increase in temperature. Once the heating is complete, the infrared heating element 58 turns off and the obturator 18 may be removed for use by the operator.

Moreover, in yet another aspect of the embodiment, the infrared heating element 58 rapidly heats to temperatures between 700° C.-1100° C. Thus, convective heating heats the air adjacent to the infrared heating element 58 to a superheated condition. While it may be possible to heat the filling material 22 to a desired temperature by both convection and infrared radiation, controlling the temperature of the obturator 18 becomes increasingly difficult at smaller distances. At relatively larger distances, the obturator 18 is further insulated from super-heated air, which makes output temperatures simpler to control with more predictable results. Therefore, in this aspect of the embodiment, a length 82 between the obturator 18 extending along the instrument axis 44 of the heating unit 40 and the infrared heating element 58 is defined such that the filling material 22 absorbs more heat from infrared radiation than from convection.

The combined features of increased distance between the filling material 22 and the infrared heating element 58, relatively large chamber 70, reflective surface 64, heat sink 66, and air vents 74a, 74b, 74c cumulatively serve to minimize the air temperature within the chamber 70, thereby reducing the effect of convective heat. For example, the filling material 22 can be heated to the proper temperature for root canal therapy in approximately 5 seconds using apparatus 10.

Additionally, such controlled heating is particularly beneficial in the event multiple obturators 18 are heated consecutively. For multiple heating cycles, the obturator 18 preferably begins to cool immediately after the infrared heating element 58 is turned off, even while within the chamber 70. To achieve immediate cooling during consecutive heating, the embodiment as shown in FIGS. 1-3 preferably maintains average air temperatures within the chamber 70 below approximately 60° C. Consecutive testing of five obturators 18 with ten seconds between each test indicates that the apparatus 10 will peak with average internal air temperatures between 30° C.-40° C.

To further control the heating of the obturator 18, a sensor 84 is placed within the chamber 70 to monitor the temperature. More specifically, the sensor 84 is a thermocouple. The sensor 84 provides feedback to the CPU 78 operatively connected to the infrared heating element 58. The CPU 78 selects the proper time and/or temperature to turn off the infrared heating element 58. For instance, an operator may choose to heat consecutive obturators 18, which increases the starting temperature of the chamber 70 and decreases the time necessary to properly heat the filling material 22. Thus, the controls include the sensor 84 for feedback to the CPU 78 to improve the overall performance of the apparatus 10.

Additionally, the CPU 78 and user interface 76 includes a material selection control element 86. More specifically, the material selection control element 86 is a material selection button 86 that is pushed to select the type of filling material 22 to be heated; however, any material selection control element 86 may be so used. Performance of the apparatus 10 is further optimized by selecting which filling material 22 is included on the obturator 18. For instance, gutta percha has different heating properties than RESILON® and this may affect heating times and temperatures. Thus, performance is optimized by selecting settings predetermined by the CPU 78 to change the amount of heating time and/or temperature of the apparatus 10 based on material properties. However, the material selection button 86, sensor 84, and other conceivable performance optimizations will be readily apparent to one skilled in the art. For instance, rather than optimizing performance by adjusting the amount of time to heat the filling material 22, the CPU may adjust the infrared radiation directed at the filling material 22.

In use during root canal therapy, the operator of the apparatus 10 may be a dentist, endodontist, or a medical assistant to the dentist or endodontist. The apparatus 10 is positioned at a convenient location within comfortable reach of the practitioner during root canal therapy. The operator places the obturator 18 onto the holder 16. The holder 16 holds the obturator 18 adjacent to the chamber 70. By so holding the obturator 18, the filling material 22 of the obturator 18 extends through the aperture 14 and into the chamber 70.

The operator selects the type of filling material 22 to be heated by the infrared heating element 58 within the chamber 70 by using a material selection control element 86. This material selection is communicated to the CPU 78. Furthermore, a sensor 84 senses the temperature within the chamber 70. The sensed temperature is also communicated to the CPU 78. Using the CPU 78, the predetermined amount of time to heat the filling material 22 is adjusted to an optimized amount of time based on the material selection and/or sensed temperature. The operator powers on the infrared heating element 58 for the optimized amount of time by pushing the button 80. Because the apparatus 10 is powered by the battery 38, the infrared heating element 58 is remotely powered. However, selecting the material and/or sensing the temperature within the chamber 70 for communication to a CPU for optimizing the predetermined amount of time is not intended to limit the invention described herein. In the alternative, the operator may simply power on the infrared heating element to heat the filling material 22 for the predetermined amount of time or use any combination of selecting the material or sensing the temperature to further optimize the apparatus 10.

The infrared heating element 58 generates heat energy, including infrared radiation. This infrared radiation is directed to the filling material 22. Moreover, infrared radiation is also reflected by the reflective surface 64 within the chamber 70, which directs additional infrared radiation to the filling material 22. Convective heat is also generated within the chamber 70 by the infrared heating element. However, the filling material 22 absorbs more infrared heat than convective heat. This softens the filling material 22 portion of the obturator 18. Once the filling material 22 is properly heated, the infrared heating element 58 turns off, the obturator 18 is removed from the apparatus 10, and the practitioner fills the root canal with softened filling material 22.

In one aspect of the embodiment, managing convective heat produced by the apparatus 10 is helpful to control the heating of the filling material 22. To manage convective heat, a portion of the heat energy from the chamber 70 is dissipated into the ambient environment by the heat sink 66 and air vents 74a, 74b, 74c. The heat sink 66 is in thermal communication with both the chamber 70 and the interior space 75. Because the chamber 70 is relatively warmer than the interior space 75, heat energy dissipates to the interior space 75. Interior air vents 74c promote interior circulation of the convectively heated air. The convectively heated air of the interior space 75 rises within the apparatus 10 and is expelled to the ambient environment through the upper air vent 74a. In addition, cool air is drawn into the interior space 75 of the apparatus 10 through the lower air vent 74b.

In another aspect of the embodiment, the operator may mistakenly drop the obturator 18 through the chamber 70 while attempting to place the obturator on the holder 16. Dropped obturators 18 are collected within the heater well 30 below the infrared heating element 58. To retrieve obturators 18, the operator removes the removable cover 42 of the heater well 30. Once the removable cover 42 is removed, the operator may access the dropped obturators 18 for removal from the apparatus 10.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be from such details without departing from the scope or spirit of the general inventive concept.

What is claimed is:

1. A method of filling a root canal with a heat softenable filling material carried on an endodontic instrument, the method comprising:
   holding the endodontic instrument with at least a filling material portion thereof extending into a chamber;
   directing infrared radiation from an infrared radiation heating element at the filling material portion within the chamber;

heating and softening the filling material portion with the radiation;

filling the root canal with the softened filling material portion;

drawing cool air from an ambient environment into the chamber through a first air vent; and expelling heated air from the chamber into the ambient environment through a second air vent.

2. The method of claim 1 further comprising:
dissipating heat from the chamber into an ambient environment with a heat sink.

3. The method of claim 1 further comprising:
reflecting the infrared radiation with a reflective surface in the chamber.

4. The method of claim 1 further comprising:
sensing a temperature within the chamber;
communicating the temperature to a CPU; and
adjusting with the CPU the amount of time that the filling material portion is heated based on the sensed temperature.

5. The method of claim 1 further comprising:
selecting with a material selection control element a type of the filling material to be heated;
communicating the selected material to a CPU; and
adjusting with the CPU the amount of time that the filling material portion is heated based on the selected material.

6. The method of claim 1 wherein the infrared radiation heating element is generally cylindrically shaped, and wherein the step of holding the endodontic instrument further comprises positioning the endodontic instrument coaxially with an axis defined by the generally cylindrically shaped infrared radiation heating element.

7. The method of claim 6 further comprising the step of reflecting the infrared radiation radially inward toward the axis with a reflective surface.

8. The method of claim 1 further comprising the step of passing the air over a plurality of fins so that the fins absorb heat and dissipate heat away from the filling material portion.

9. The method of claim 1 further comprising the steps of:
calculating at least one of a predetermined temperature for the infrared radiation heating element and a predetermined amount of time for energizing the infrared radiation heating element; and
energizing the infrared radiation heating element to at least one of the predetermined temperature and for the predetermined time.

10. The method of claim 9 further comprising the steps of:
measuring a temperature inside the chamber; and
adjusting at least one of the predetermined temperature and predetermined time based at least in part on the measured temperature.

11. The method of claim 1 wherein the heating and softening of the filling material portion is primarily due to infrared heating.

12. A method of filling a root canal with a heat softenable filling material carried on an endodontic instrument, the method comprising:
providing an apparatus having a housing, an infrared radiation heating element in the housing, an air inlet in the housing below the infrared radiation heating element, and an air outlet in the housing above the infrared radiation heating element, holding the endodontic instrument with at least a filling material portion thereof extending into the housing;

directing infrared radiation from the infrared radiation heating element at the filling material portion so as to soften the filling material portion with infrared heat from the infrared radiation heating element;

cooling an interior of the housing with natural convection by passing air in to the housing through the air inlet, upwardly through the housing, and out of the housing through the air outlet, to remove convective heat from the housing generated by the infrared radiation heating element so as to reduce softening of the filling material portion due to convective heat generated by the infrared radiation heating element;

the heating and softening of the filling material portion thereby being primarily due to infrared heating; and filling the root canal with the softened filling material portion.

13. The method of claim 12 further comprising:
dissipating heat from the housing into an ambient environment with a heat sink.

14. The method of claim 12 further comprising:
reflecting the infrared radiation with a reflective surface in the housing.

15. The method of claim 12 further comprising:
sensing a temperature within the housing;
communicating the temperature to a CPU; and
adjusting with the CPU the amount of time that the filling material portion is heated based on the sensed temperature.

16. The method of claim 12 further comprising:
selecting with a material selection control element a type of the filling material to be heated;
communicating the selected material to a CPU; and
adjusting with the CPU the amount of time that the filling material portion is heated based on the selected material.

17. The method of claim 12 wherein the infrared radiation heating element is generally cylindrically shaped, and wherein the step of holding the endodontic instrument further comprises positioning the endodontic instrument coaxially with an axis defined by the generally cylindrically shaped infrared radiation heating element.

18. The method of claim 17 further comprising the step of reflecting the infrared radiation radially inward toward the axis with a reflective surface.

19. The method of claim 12 further comprising the step of passing the air over a plurality of fins so that the fins absorb heat and dissipate heat away from the filling material portion.

20. The method of claim 12 further comprising the steps of:
calculating at least one of a predetermined temperature for the infrared radiation heating element and a predetermined amount of time for energizing the infrared radiation heating element; and
energizing the infrared radiation heating element to at least one of the predetermined temperature and for the predetermined time.

21. The method of claim 20 further comprising the steps of:
measuring a temperature inside the housing; and
adjusting at least one of the predetermined temperature and predetermined time based at least in part on the measured temperature.

* * * * *